(12) United States Patent
Hooton

(10) Patent No.: US 9,681,878 B1
(45) Date of Patent: Jun. 20, 2017

(54) MULTI-USE TOURNIQUET

(71) Applicant: Lisa K. Hooton, Murray, UT (US)

(72) Inventor: Lisa K. Hooton, Murray, UT (US)

( * ) Notice: Subject to any disclaimer, the term of this patent is extended or adjusted under 35 U.S.C. 154(b) by 551 days.

(21) Appl. No.: 14/046,802

(22) Filed: Oct. 4, 2013

(51) Int. Cl.
*A61B 17/132* (2006.01)

(52) U.S. Cl.
CPC .................. *A61B 17/1322* (2013.01)

(58) Field of Classification Search
CPC ................................................. A61B 17/1322
See application file for complete search history.

(56) References Cited

U.S. PATENT DOCUMENTS

| | | | | |
|---|---|---|---|---|
| 3,930,506 A | * | 1/1976 | Overend | A61B 17/1322 606/203 |
| 5,540,714 A | * | 7/1996 | Payne, Jr. | A61B 17/1322 606/201 |
| 2003/0028215 A1 | * | 2/2003 | Brooks | A61B 17/1327 606/203 |
| 2011/0271494 A1 | * | 11/2011 | Bellamy | A44B 11/18 24/16 R |

* cited by examiner

*Primary Examiner* — Corrine McDermott
*Assistant Examiner* — Tin Nguyen
(74) *Attorney, Agent, or Firm* — Brian C. Trask

(57) ABSTRACT

A multi-use tourniquet that may be first used in conventional manner to draw blood from an extremity, then reused as a compressor for a bandage applied to the resulting wound. The tourniquet includes a band of stretchy elastic material, typically carrying an adhesive that can attach to the surface of the band at a plurality of locations effective to constrict a circumference of the extremity. Desirably, the tourniquet is structured such that no adhesive is applied to the skin of the patient during use of the tourniquet. Certain tourniquets may carry decorative surface ornamentation.

5 Claims, 2 Drawing Sheets

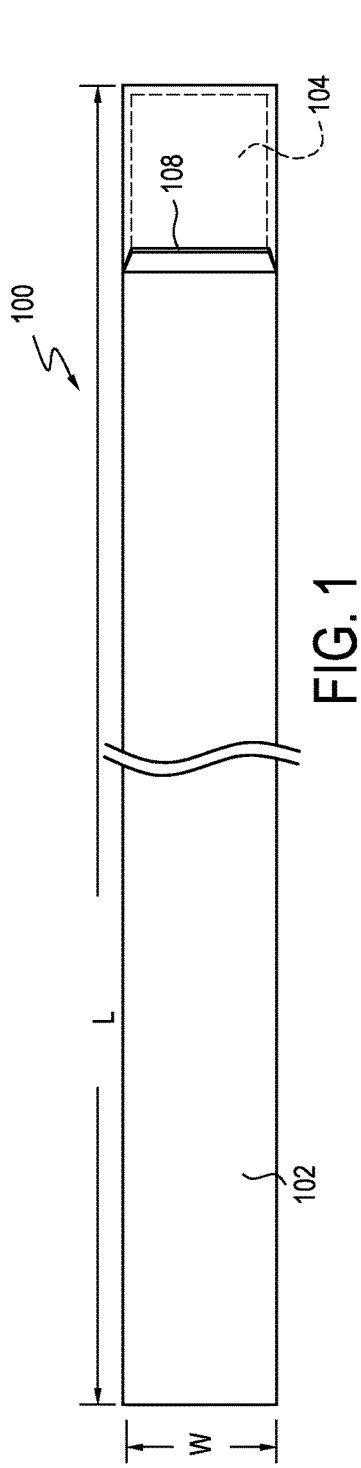
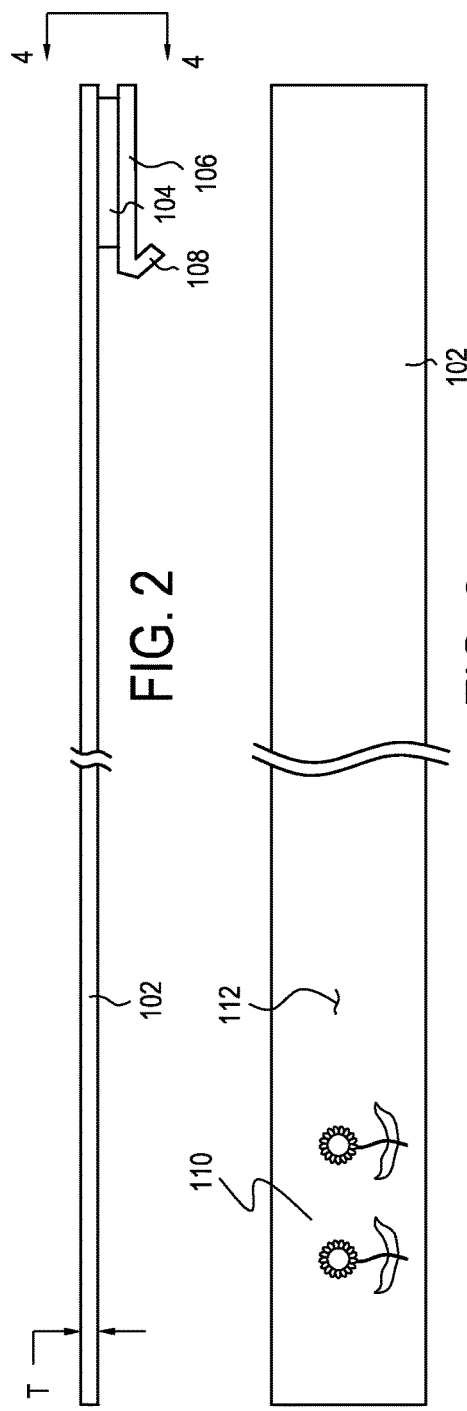
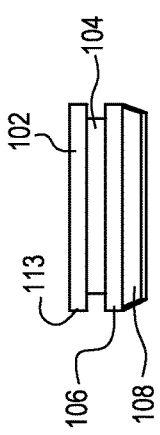
FIG. 1
FIG. 2
FIG. 3
FIG. 4

MULTI-USE TOURNIQUET

BACKGROUND

Field of the Invention

This invention relates to medical devices. It is particularly directed to a multi-use tourniquet for exemplary use in phlebotomy.

State of the Art

It is known in the field of phlebotomy to apply an elastic membrane tourniquet to resist flow of venous blood prior to drawing a blood sample using, for example, a syringe and needle. One such ubiquitous tourniquet consists of a membrane-like band of rubber-like material that is less than about $1/16$ inches in thickness, about 1 inch wide, and about 18 inches long. Application of the tourniquet improves needle access to the target vein, and facilitates collection of an ample blood sample in short order.

The ubiquitous phlebotomy tourniquet is conventionally applied to a human limb, e.g. an arm, by wrapping the band in stretched condition around the circumference of the arm to over-wrap and thereby trap a first end of the band against the arm. The over-wrapping portion of the band essentially anchors the trapped end using friction and compression of the trapped first end against the skin. A stretched condition may be conveniently maintained in an encircling portion of the band by twisting and tucking a proximal end portion under a retention wrap of the band effective to hold the proximal end portion at a second anchored position. Again, compression from the encircling portion and friction hold the second end in an installed position. The stretched and anchored band compresses onto the skin around the circumference of the arm, and resists flow of venous blood. Typically, a tail of the band's second end is arranged to protrude from under the retention wrap to facilitate removal of the anchored proximal portion from under the retention wrap. A yank on the tail can extract the tucked portion from under the retaining wrap.

After a medical procedure (e.g., a blood draw) is performed, the tourniquet may be removed by simply pulling on the protruding tail, and a bandage is applied to the sample access wound. A conventional bandage includes an adhesive strip sized between perhaps about 3 and about 6 inches in length and about 1 to 2 inches in width that is applied directly to the skin of the patient. The length generally extends partially around the circumference of the arm, and the strip is typically applied in a state of tension to place compression onto the wound. Conventionally, pressure is also applied by the patient for a period of time to assist in wound closing.

The above-described ubiquitous phlebotomy tourniquet was conventionally re-used a plurality of times, on a plurality of different patients. Essentially, the tourniquet band was re-used until its resiliency deteriorated to an ineffective condition. However, a change in best medical practice many years ago (with respect to the filing date of this document) required that such medical tools be used on only a single patient, and then discarded. It is believed that single-patient use was promulgated to avoid cross-contamination between patients.

There are undesirable effects resulting from the above-described conventional phlebotomy treatment that have been long-known, and unresolved by others. For example, removing the adhesive strip from a patient's skin can be painful, and even traumatic. In the case of certain elderly individuals, removal of the adhesive strip can actually tear the skin. Sometimes, application of operable pressure is not maintained for a sufficient length of time, resulting in blood loss and/or extensive bruised-appearing areas or blood clots. Adhesive on the bandage strip may cause an allergic reaction. If the conventional tourniquet described above is applied to additionally compress the wound, an elderly patient may not be able to remove it, due to low hand strength, or other reason. Long-term application of a tourniquet can be fatal to extremity tissues.

Tourniquets of various sorts are known. Such devices operate to resist flow of blood through a portion of a body circumscribed by the device, typically an extremity. Even a simple rope, or other relatively non-elastic member, may suffice as an operable tourniquet. In use of non-elastic devices, such as a length of rope, a compression must be induced by an external operator. For example, a stick may be inserted into a loop of rope, and the stick may be rotated to cause the rope to wind up, and thereby compress an encircled extremity. An external operator is required to maintain an effective compression on the encircled body portion. For example, tucking a second end of rope under an encircling portion of rope would be inoperable to maintain a sufficient compression around an encircled extremity, because the non-elastic rope does not inherently produce a sufficient self-biased constriction.

A commercially available alternative tourniquet that is characterized as being non-elastic includes a plastic strap similar to an industrial-sized zip tie. That device is advertised on the internet for military use as a tourniquet. The plastic strap that carries the teeth is not very elastic and stretchy (e.g. is probably subject to plastic deformation or damage beyond less than 10% elongation). Tension applied to the strap basically compresses tissues directly, and those tissues generate the tension bias remaining in the strap after its installation. Such a tourniquet is tightened in a ratchet-like fashion, by pulling the end through an opening carried at one end, and teeth disposed along the length of the band are successively engaged by a pawl associated with the opening. Friction between the plastic band segments would be inoperable to maintain an effective tension in the band if a proximal portion were tucked under an encircling length of the band, similar to a conventional phlebotomy procedure. It is not clear that the plastic band could even be manipulated to form the conventional twist-and-tuck-under proximal portion to expose a tail end. It is believed that the plastic band must be cut with a tool to remove the tourniquet from the patient's extremity. In short, the known tourniquets are incapable of performing certain desired actions.

BRIEF SUMMARY OF THE INVENTION

This invention provides an apparatus, including an elongate band and a fastener. One workable elongate band is structured as an elastic membrane having a length in excess of about one foot. Desirably, the band has sufficient elastic resilience that, when the band is stretched along its length axis and wrapped around a human limb, tension inherent in the band causes a constriction on the limb sufficient to resist venous blood flow in the limb. A currently preferred band is structured to permit wrapping in stretched condition around the entire circumference of a human arm to over-wrap a trapped end of the band, and then to permit anchoring the free end of the band by tucking a proximal free portion under a wrapped length of the band effective to maintain a stretched condition in a portion of the band.

Certain embodiments include a band having a length sized between about 12 inches and about 24 inches, and a width sized between about ½ inch and about 2 inches. An operable band is formed from a material capable of stretching by at least 50 percent under influence of a load applied along the band's length axis, and subsequently returning to its original length when the load is removed. A workable band may be formed from a material having elastic properties similar to rubber. Preferably, the band is hypo-allergenic.

A workable fastener is typically carried at a first end of the band. Preferably, the fastener is adapted to form a connection between the first end and only a surface of the band at a selected one of a plurality of locations spaced apart along the band's length axis. The currently preferred fastener includes an adhesive element. One workable fastener includes a tear-off element structured to resist inadvertent exposure of the adhesive. When present, it is desirable for the tear-off element to be removable in a tool-free operation to prepare the tourniquet for forming a subsequent connection between the adhesive and the surface of the band. A workable fastener includes a length of double-sided tape.

A method for using an apparatus structured as described above includes: wrapping the band in stretched condition around the circumference of a human limb to over-wrap and thereby trap a first end of the band against the limb effective to anchor the first end; maintaining a stretched condition in a length of the band by tucking a proximal end portion under a wrap of the band effective to hold the proximal end portion at an anchored position; performing a medical procedure on the limb; removing the proximal end portion from its anchored position and freeing the band from engagement with the limb; applying a bandage to the limb; wrapping the band in stretched condition over the bandage and continuing around the entire circumference of the limb to over-wrap and thereby trap one end of the band against the limb; and affixing the fastener to only a surface of the band at a location effective to maintain pressure on the bandage.

One aspect of the invention provides a method for drawing a sample of blood from a human patient. In a first step, a tourniquet is applied to an extremity of a human body to facilitate acquisition of the blood sample. Then, the tourniquet is removed for a first time. A dressing is then applied over the sample access wound, and the tourniquet is applied for a second time to apply compression onto the dressing for a period of time. Subsequent to expiration of the period of time, the tourniquet is removed for a second time.

Sometimes, applying the tourniquet for a first time includes wrapping the tourniquet in stretched condition around the circumference of a human limb to over-wrap and thereby trap one end of the tourniquet against the limb effective to anchor that end, and maintaining a stretched condition in a length of the tourniquet by tucking a proximal end portion under a wrap of the tourniquet effective to hold the proximal end portion at an anchored position. Applying the tourniquet for a second time may include wrapping the tourniquet in stretched condition over the dressing and continuing around the entire circumference of the extremity to over-wrap and thereby trap a first end of the tourniquet against the extremity effective to anchor that end, and affixing a fastener, carried by the tourniquet proximal to a second end of the tourniquet, to only a surface of the tourniquet at a location effective to maintain compressive pressure on the dressing.

Removing the tourniquet for a first time may conveniently include grasping a protruding tail end of the tourniquet and pulling the tail end transverse to the wrap effective to remove the proximal portion from anchored engagement under the wrap. Removing the tourniquet for a second time may include grasping a free edge of band material and peeling the adhesive from attachment to the surface.

BRIEF DESCRIPTION OF THE DRAWINGS

In the drawings, which illustrate what are currently considered to be the best modes for carrying out the invention:

FIG. 1 is a plan view of one side of a currently preferred embodiment structured according to certain principles of the invention;

FIG. 2 is a side view of the embodiment illustrated in FIG. 1;

FIG. 3 is an end of the embodiment illustrated in FIG. 2, taken at section 4-4 and looking in the direction of the arrows;

FIG. 4 is a plan view of the other side of the embodiment illustrated in FIG. 1;

DETAILED DESCRIPTION OF THE ILLUSTRATED EMBODIMENTS

Figure 5:
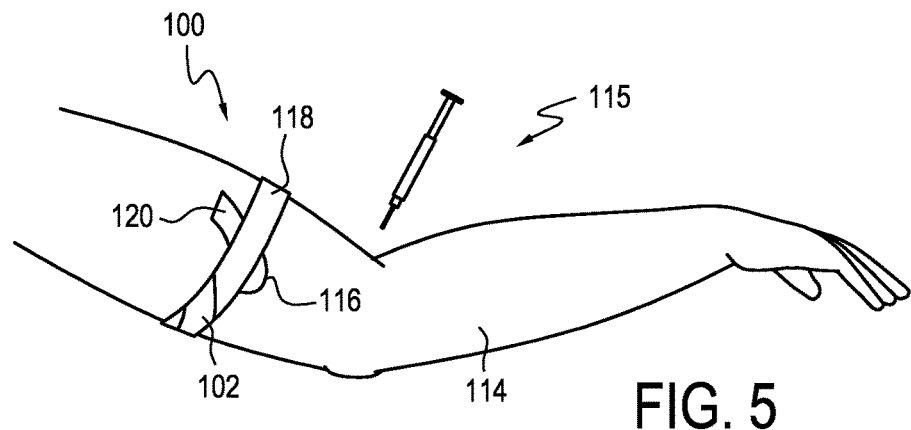
FIG. 5 illustrates the embodiment of FIG. 1 in use as a tourniquet.

Reference will now be made to the drawings in which the various elements of the illustrated embodiments will be given numerical designations and in which the invention will be discussed so as to enable one skilled in the art to make and use the invention. It is to be understood that the following description is only exemplary of the principles of the present invention, and should not be viewed as narrowing the claims which follow.

As illustrated in FIGS. 1-4, one embodiment of a tourniquet, generally 100, according to certain principles of the invention may include an elongate band 102, and an adhesive element 104. A workable band 102 has sufficient elasticity to permit stretching the band 102 in a length direction, application of the band 102 to encircle an extremity, and anchoring opposite ends of the band operably to apply a constriction onto that extremity sufficient to at least resist flow of venous blood past the constricted site.

Certain operable bands are made from rubber, or rubber-like materials, such as silicone rubber, TPE, and latex, and other medical-grade materials. Preferably, a band 102 is formed from an elastic material capable of stretching by at least 50 percent under influence of a load applied along said length axis, and subsequently returning to its original length when that load is removed. One exemplary and currently preferred band 102 is made from a latex-free medical grade rubber, or rubber-like compound, which is inherently hypo-allergenic. Desirably, the band is made from a membrane, or membrane-like material that can easily be bent transversely to facilitate wrapping the band around an extremity of a human patient. It is further desirable that the band is structured to permit its twisting (e.g. approximately around its length axis) and out-of-plane bending to permit anchoring a folded section of the band under a wrapped length of the band.

With reference to FIGS. 1 and 2, an exemplary band 102 may have a width W between about ½ inches and about 2 inches, a length L of between about 12 inches and about 24 inches, and a thickness T between about 0.01 inches and 0.1 inches. A currently preferred band 102 has a length L of about 18 inches, a width W of about 1 inch, and a thickness T of about 1/32 inches. Bands having other sizes are also workable. A workable band shape is rectangular, although such shape is not required. Bands may have any desired plan form shape, including oval, rectangular, or any other desired substantially elongate shape. A constant width, length, and/or thickness is not required.

It is within contemplation that embodiments structured according to certain principles of the invention may include a band that is decorated to present an ornamental appearance. For purpose of this disclosure, decorative surface ornamentation is defined as being in contrast to a single solid color that is found in commercially available tourniquets. As non-limiting examples, a band may include a plurality of different colors; one or more shapes that is/are differently colored than a background; cartoon characters; animals; flowers; balloons, and the like. FIG. 3 illustrates exemplary decorative surface ornamentation, generally indicated at 110, including a plurality of flowers carried on surface 112. Certain embodiments may include gender-coded colored elements or background, such as pink for girls, and blue for boys. Sometimes, it may be desirable for an embodiment to substantially match the flesh tone of a patient.

An operable adhesive element 104 simply permits anchoring one end of the tourniquet to a length of that tourniquet at a location disposed at a plurality of potentially desired locations spaced apart along the length of the band 102. A length of double-sided tape may form an exemplary and operable adhesive element 104. Desirably, the adhesive element is formed from a compound that is hypo-allergenic, to avoid irritation to a patient in the event that adhesive does inadvertently make contact with that patient's skin. As seen in FIGS. 1 and 4, a preferred adhesive element is sized smaller than the width of the band 102 to provide a free edge 113 that can be grasped to facilitate separation of a joint made between the adhesive 104 and a portion of band 102 upon anchoring the tourniquet in an installed position.

Desirably, an optional and easily removed cover 106 is included to maintain integrity of the adhesive element 104 during storage. A workable cover 106 has only a small adherence to the adhesive, and, subsequent to removal of the cover 106, leaves behind adhesive in a state that permits adhesion of the remaining adhesive to a surface. It is further desirable to include provision to easily remove the cover 106 in a tool-free operation, such as by way of an extended (and optionally folded) end 108 that can easily be grasped by a medical practitioner.

FIG. 5 illustrates an embodiment of the invention in use during a medical procedure, generally indicated at 115. The tourniquet 100 is installed on arm 114 for a first time by wrapping the tourniquet in stretched condition around the circumference of arm 114 to over-wrap, and thereby trap one end of tourniquet 100 against the arm effective to anchor that one end. Then, the stretched condition is maintained in a portion of tourniquet 100 by tucking a proximal end portion 116 under a wrap 118 of the tourniquet effective to hold that proximal end portion 116 at an anchored position. Desirably, a tail end 120 is disposed protruding transversely from the wrap 118 to facilitate removal of the tourniquet. The tucked portion may be selected at a convenient point along the length of a tourniquet, e.g. if the patient's arm is skinny, the protruding tail 120 may be much longer than for a large-diameter arm. In any case, and subsequent to performing the desired medical treatment, the tail end 120 may then simply be pulled in a transverse direction to the wrap to free the trapped proximal portion 116 and remove the tourniquet 100.

Figure 6:
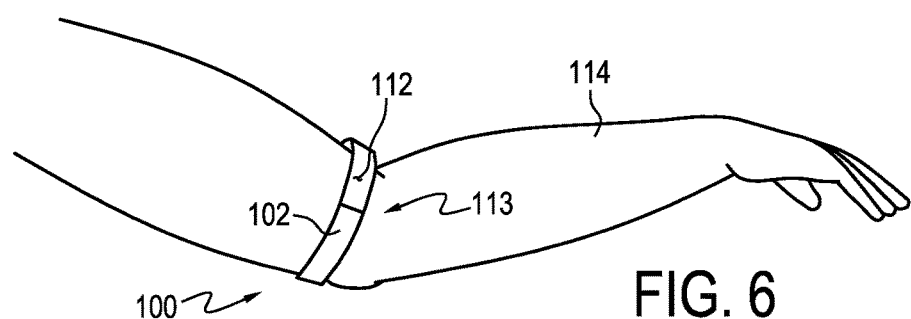
FIG. 6 illustrates the embodiment of FIG. 1 in use as a bandage (or dressing) compressor.
Figure 7:
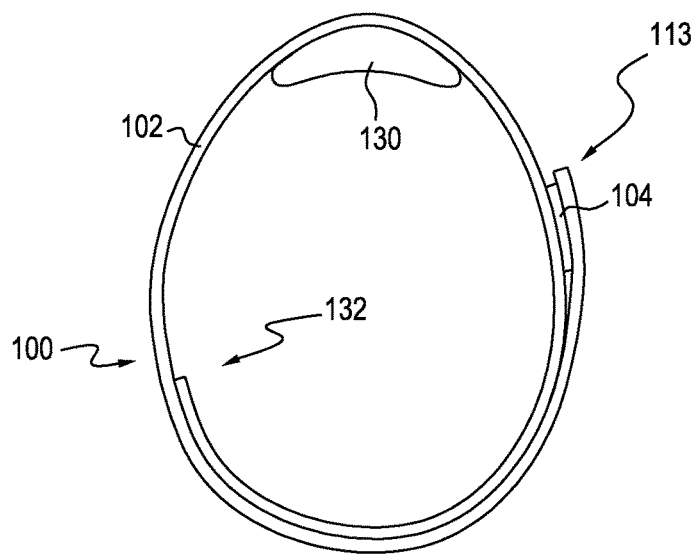
FIG. 7 is an end view of the embodiment illustrated in FIG. 6, but with the arm removed.

FIGS. 6 and 7 illustrate tourniquet 100 installed for a second time as a compressor effective to apply pressure onto a bandage or dressing 130. An exemplary dressing 130 may include, for non-limiting examples, a gauze pad or cotton ball. The trapped end that forms a first anchor for one end of the tourniquet is generally indicated at 132 in FIG. 7. The second anchor for the opposite end of tourniquet 100 desirably includes a free edge, generally indicated at 113, to facilitate separation of adhesive 104 from its attachment at a desired location on surface 112. Desirably, all of the adhesive 104 is in contact with only surface 112, and no adhesive is in contact with the patient's skin.

Embodiments of the invention may be manufactured in a reel-to-reel process, with individual lengths of band material 102 being connected end-to-end by a perforated and separable joint. An adhesive element 104 and cover 106 may be applied by way of an in-line process to one end of each tourniquet 100, and a desired length (and corresponding number) of the linked tourniquets 100 may be spooled onto a reel for packaging and sale. Alternatively, tourniquets 100 may be individually packaged, as desired.

While the invention has been described in particular with reference to certain illustrated embodiments, such is not intended to limit the scope of the invention. The present invention may be embodied in other specific forms without departing from its spirit or essential characteristics. The described embodiments are to be considered as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for using an elongate band structured as an elastic membrane having a length in excess of about one foot, the band having elastic resilience so that, when the band is stretched along its length axis and wrapped around a human limb, tension inherent in the band causes a constriction on the limb sufficient to resist venous blood flow in the limb, with a fastener carried at one end of the band, the fastener being adapted to form a connection between the one end and only a surface of the band at a selected one of a plurality of locations spaced apart along the length axis, the method comprising in the following order:
   a) wrapping the band in stretched condition around the circumference of a human limb to over-wrap and thereby trap one end of the band against the limb effective to anchor the one end;
   b) maintaining a stretched condition in a portion of the band by tucking a proximal end portion under a wrap of the band effective to hold the proximal end portion at an anchored position;
   c) performing a phlebotomy procedure on the limb;
   d) removing the proximal end portion from the anchored position and freeing the band from engagement with the limb;
   e) applying a bandage to the limb;
   g) wrapping the band in stretched condition over the bandage and continuing around the entire circumference of the limb to over-wrap and thereby trap one end of the band against the limb; and
   g) affixing the fastener to only a surface of the band at a location effective to maintain pressure on the bandage.

2. A method, comprising:
   applying a tourniquet to an extremity of a human body to facilitate acquisition of a blood sample, the tourniquet being structured as an elastic membrane having a length in excess of about one foot, the band having elastic resilience so that, when the band is stretched along its length axis and wrapped around a human limb, tension inherent in the band causes a constriction on the limb sufficient to resist venous blood flow in the limb, with a fastener carried at one end of the band, the fastener being adapted to form a connection between the one end and only a surface of the band at a selected one of a plurality of locations spaced apart along the length axis of the band;

removing the tourniquet for a first time;

applying a dressing over a sample access wound;

applying the tourniquet for a second time to apply compression onto the dressing for a period of time; and subsequent to expiration of the period of time, removing the tourniquet for a second time, wherein:

applying the tourniquet for a second time comprises wrapping the tourniquet in stretched condition over the dressing and continuing around the entire circumference of the extremity to over-wrap and thereby trap one end of the tourniquet against the extremity effective to anchor the one end and affixing a fastener, carried by the tourniquet proximal to a second end of the tourniquet, to only a surface of the tourniquet at a location effective to maintain compressive pressure on the dressing.

3. The method according to claim 2, wherein:

applying said tourniquet for a first time comprises wrapping said tourniquet in stretched condition around the circumference of a human limb to over-wrap and thereby trap one end of said tourniquet against said limb effective to anchor said one end; and maintaining a stretched condition in a portion of said tourniquet by tucking a proximal end portion under a wrap of said tourniquet effective to hold said proximal end portion at an anchored position.

4. The method according to claim 3, wherein:

removing said tourniquet for a first time comprises grasping a protruding tail end of said tourniquet and pulling said tail end transverse to said wrap effective to remove said proximal portion from anchored engagement under a wrap.

5. The method according to claim 2, wherein:

said fastener comprises an adhesive element; and removing said tourniquet for a second time comprises grasping a free edge of band material proximal to said second end, and peeling said adhesive from attachment to said surface.

\* \* \* \* \*